United States Patent [19]

Bailey et al.

[11] Patent Number: 4,720,286

[45] Date of Patent: Jan. 19, 1988

[54] MULTIFOCUS INTRAOCULAR LENS

[76] Inventors: Kelvin E. Bailey, 1100 Greentree Ct., Lexington, Ky. 40502; Daniel B. Pope, 203 69th St., NW., Bradenton, Fla. 33529

[21] Appl. No.: 632,863

[22] Filed: Jul. 20, 1984

[51] Int. Cl.$^4$ ............................................. A61F 2/16
[52] U.S. Cl. ...................................................... 623/6
[58] Field of Search ............................................. 623/6

[56] References Cited

U.S. PATENT DOCUMENTS

| | | |
|---|---|---|
| 2,437,642 | 3/1948 | Henroteau . |
| 3,598,479 | 8/1971 | Wright . |
| 3,614,215 | 10/1971 | Mackta . |
| 4,010,496 | 3/1977 | Neefe . |
| 4,174,156 | 11/1979 | Glorieux . |
| 4,373,218 | 2/1983 | Schachar . |
| 4,512,040 | 4/1985 | McClure ............................ 623/6 |

FOREIGN PATENT DOCUMENTS 90030 11/1960 Denmark .
1279252 11/1961 France .

*Primary Examiner*—V. Millin
*Attorney, Agent, or Firm*—Finnegan, Henderson, Farabow, Garrett & Dunner

[57] ABSTRACT

An intraocular lens that internally alters its focal length with the position of the eye with respect to the horizontal. The lens is comprised of a solid transparent material having a hollow lenticule that encompasses the optical zone of the eye. The lenticule is connected with fluid reservoirs above and below it, and the reservoirs also are interconnected by channels on both sides of the lenticule. By moving fluids of different indices of refraction through the lenticule, the lens can be made to change its power. When the eye is in the horizontal position, the index of refraction of the fluid occupying the lenticule is such that distant objects are in focus, and when the eye is inclined 45°–90° from the horizontal as for reading, the index of refraction of a different fluid occupying the lenticule is such that near objects are in focus.

9 Claims, 10 Drawing Figures

MULTIFOCUS INTRAOCULAR LENS

BACKGROUND OF THE INVENTION

This invention relates to an intraocular lens, and more specifically to an intraocular lens that internally alters its focal length.

Lenses are optical devices that bend light. The angle at which the light is bent is determined by: (1) the angle of incidence of the light wave; (2) the specific wave length; and (3) the refractive indices (n) of all the mediums through which it passes. Using Schnell's law, the refracting power of a lens system can be obtained. The power is determined by the change in n of the refractive media at their interfaces and their surface shape characteristics. In a lens system, the power of the system is determined by all the refracting interfaces and all the differences in n. The power of the lens system can be changed by altering the curvature of the lenses or the index of refraction of one or more parts of the system or both. In conventional systems, the effective power of the system is changed by mechanically changing the separation of one or more solid lenses.

Single lenses generally are of a fixed focal length. Fused bifocal lenses and aspheric lenses have two or more optical focal planes that are engaged by changing the relationship of the light path or the observer to the lens. All such lenses require movement of either the lens, light path, or observer to engage a different focal plane. Without moving the lens in relationship to the light path, the focal length of fused bifocals and aspheric lenses can not be altered.

The natural lens of the eye is a single lens with a variable focal length. The focal length is changed by muscles in the eye that change the shape of the lens. Thus, this natural lens does not require a movement in the position of the lens, the light path, or the observer to achieve a change in focal length.

Removal of the natural lens by surgery necessitates its replacement with glasses, a contact lens, or an intraocular lens. The first intraocular lens was inserted in 1949 by Ridley in London. It consisted of a solid lenticle with one focal point. Since that time all intraocular lenses, including those currently being implanted, whether anterior chamber, posterior chamber, or iris supported, have had a solid plastic lenticle with a single focal point.

Recent developments have dealt primarily with (1) ultraviolet protection, (2) flexible support, (3) flexible lenticle and haptics, and (4) laser ridge for the posterior capsule. None of these address a major disadvantage of present intraocular lenses, which is the fact that they cannot change focal length on demand.

A recent U.S. patent to Schachar (U.S. Pat. No. 4,373,218) discloses the use of an extra-scleral fluid reservoir to inflate and deflate a flexible posterior chamber lens in order to vary the power of the lens. This lens has at least four major disadvantages: (1) a permanent communication exists between the intraocular structures and the extraocular reservoir, which, along with the lens' electronics, increases the risk of infection and inflammation; (2) it requires an electrical source and microprocessor, which are subject to electrical failure; (3) it is dependent on an electrical pump and valve system, which are subject to mechanical wear and failure; and (4) it is not self-contained.

U.S. Pat. No. 4,010,496 to Neefe is for a bifocal intraocular lens that is solid and depends on an intact pupil and iris support. The wearer of this lens will have bifocal vision when his pupil is dilated; the lower part of the lens will be available for near vision and the upper part will be available for far vision. The wearer will have far vision only, when his pupil is constricted and the lower part of the lens is closed off. This situation is nonphysiologic in at least two circumstances. First, under normal reading conditions, a person reads under bright light, causing the pupil to constrict. A person reading under these conditions would not be able to use the part of the Neefe lens designed for near vision. Second, under conditions of low light, the pupil is dilated. The wearer of the Neefe lens will have near vision instead of far vision under these circumstances, even when looking straight ahead. Finally, this lens could lead to visual confusion from having the bifocal plane split the field of vision by dividing the retina, which, in turn, could lead to diplopia and/or glare.

Intraocular lenses are now implanted after cataract surgery in over 70% of the cases. The lenses that currently are being implanted are all fixed focal length. They are made of solid plastic, and they do not adjust for near and far vision. Thus, the power of the eye must be altered by external lenses. Moreover, the removal of the natural lens leaves the eye with no means to focus at different distances. Thus, bifocal lenses are necessary for close work.

SUMMARY OF THE INVENTION

The invention described herein provides means for obviating the above-stated problems of current intraocular lenses. The present invention is a more physiologic intraocular lens that adjusts its optical zone for near and far vision without external modification such as glasses or contact lenses, or externally supplied power, such as from a battery.

The present invention is a multifocus intraocular lens comprising a body of transparent material suitable for permanent placement in the eye; a hollow lenticule in the body, the lenticule being positioned for encompassing the light path between the pupil of the eye and the retina; a pair of fluid reservoirs in the body, one above and one below the lenticule and in fluid communication therewith; channel means for interconnecting the reservoirs, bypassing the light path and the lenticule and forming a closed system within the body; and a transparent fluid means filling the closed system for changing the index of refraction of the lens upon predetermined changes in the inclination of the light path with respect to the horizontal.

The important advantage of this invention is that it provides maintenance free visual correction without external devices after the natural lens has been removed from the eye. It adjusts focal lengths between near and far vision when the wearer of the lens follows the natural inclination to look down for near vision, such as needed for reading, or to look to the distance for far vision. This method of adjustment is unlike that for bifocal or trifocal lenses where the wearer must learn to look through various areas of the lens to get the needed correction. The adjustment is accomplished by moving fluids of different n through the optical zone, whereby the effective power of the lens is altered without altering the light path through the lens, the curvature of the lens, the distance separating the lens elements, or the distance from the focal plane. As a result, the lens will focus on near objects when the eye is in the normal reading position (i.e., 45-90 degrees from horizontal)

and will focus at infinity when the eye is in the level (horizontal) position. Thus, the patient will have the opportunity for more physiologic vision without external devices, such as glasses or contact lenses.

Another important advantage of this invention is that the adjustment occurs without moving parts, except for the flow of one or more fluids. Thus, there are no moving parts to wear out, break, get out of alignment, or break loose and move about in the eye.

In addition, the whole lens system is fixed in place, which prevents damage to other ey structures by touching or abrading them.

Additional objects and advantages of the invention will be set forth in part in the description that follows and, in part, will be obvious from the description or may be learned by the practice of the invention. The objects and the advantages of the invention may be realized and attained by means of the instrumentalities and combinations particularly pointed out in the appended claims.

The accompanying drawings, which are incorporated in and constitute a part of this specification, illustrate at least one embodiment of the invention and, together with the description, serve to explain the principles of the invention.

BRIEF DESCRIPTION OF THE DRAWINGS

The present invention can be more completely understood by reference to the accompanying drawings, in which.

DETAILED DESCRIPTION OF THE INVENTION

Figure 1:
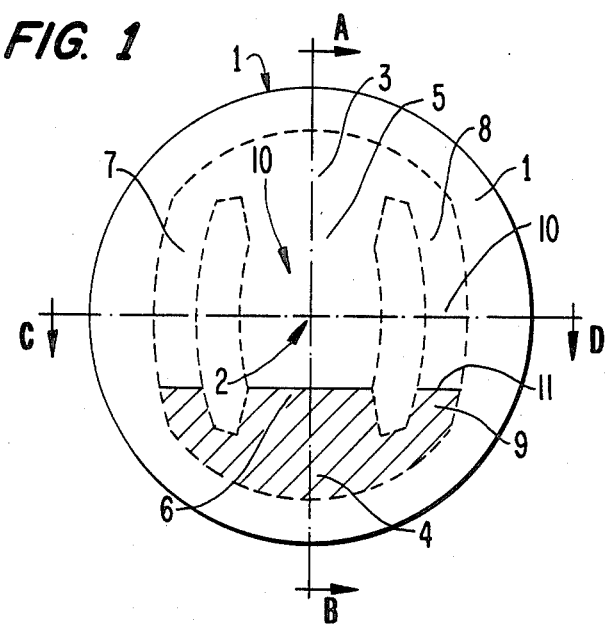
FIG. 1 is an anterior view of the preferred embodiment of the invention.
Figure 2:
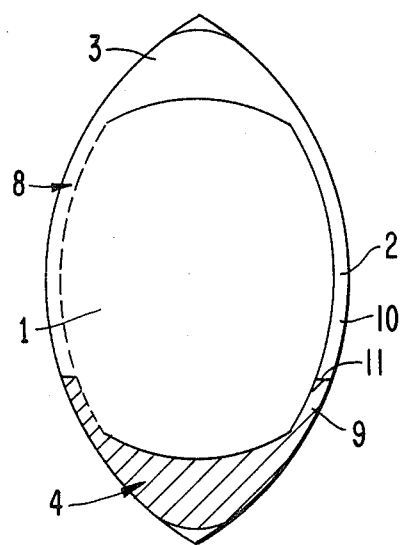
FIG. 2 is a side view along line A-B of FIG. 1.
Figure 3:
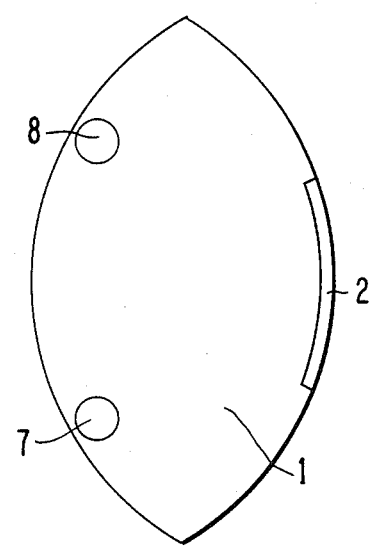
FIG. 3 is a top view along line C-D of FIG. 1.

As shown in FIG. 1, the lens 1 is comprised of a body of solid, transparent material containing a hollow lenticule 2 in fluid communication with reservoirs above 3 and below 4 the lenticule via channels above 5 and below 6 the lenticule. The reservoirs are also in fluid communication with each other through two channels 7 and 8, one on each side of the lenticule. As shown in FIGS. 2 and 3, the channels 7, 8 are posterior to the lenticule, which is adjacent the anterior surface of the transparent, solid body 1. However, the lens also could be constructed with the lenticule adjacent to the posterior surface of the transparent, solid body and the channels anterior to the lenticule. The lens shape and the lenticule shape will vary with the applications and powers desired. The shapes include, but are not limited to, plano convex, biconvex, biconcave, and concave convex. In the preferred embodiment, the lens is approximately 6-8 mm in diameter and 2-4 mm in thickness, the lenticule is approximately 3-5 mm in diameter, and the channels are approximately 0.25-0.50 mm in diameter.

The lens may be constructed out of plastic or any other material compatible with the eye. Polymethylmethacrylate is a preferred material because it is approved for use in intraocular lenses.

Figure 4A:
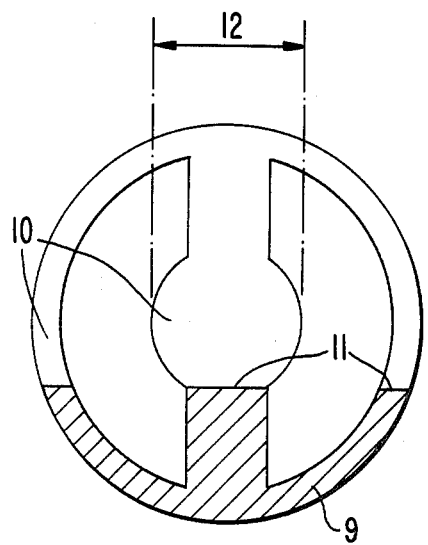
FIGS. 4A, 4B, 4C, and 4D are schematic drawings showing the movement of the fluids through the lens.
Figure 4C:
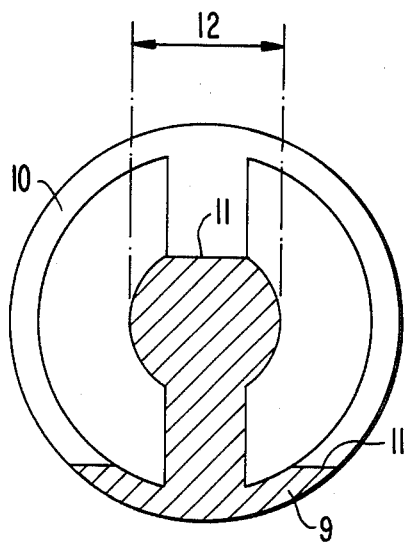
Figure 4B:
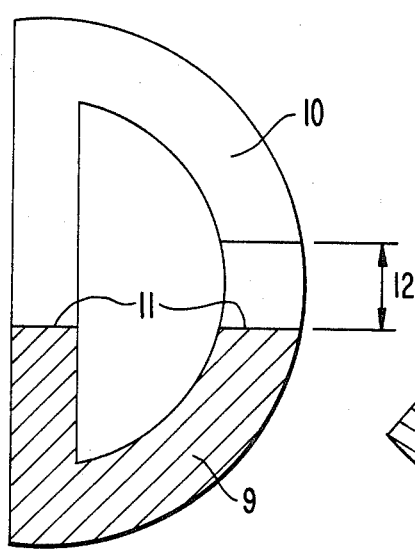
Figure 4D:
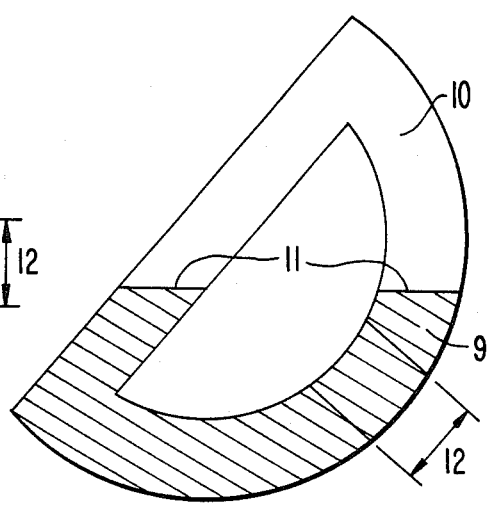

By moving fluids of different powers of refraction (n) through the hollow lenticule, the lens can be made to change power. This is accomplished, as shown in FIGS. 1 and 2, by placing two immiscible fluids of different densities 9 and 10 in the system so that a stable plane of separation 11 between the fluids is formed at the bottom of the hollow lenticule, when the light path is horizontal. In the system of channels of the invention, the position of the lens in relation to the horizontal determines which fluid fills the hollow lenticule. Gravity provides the means of moving the fluid through the channels, and the act of tilting the head provides the motive force. As shown in FIGS. 4A and 4B, when the lens is in the horizontal position, the stable plane of separation 11 is immediately below the optical zone 12, i.e. the light path, encompassed by the lenticule. The light rays pass through fluid 10, which has an n such that distant objects will be in focus. When the lens is tilted downward 45°-90° from the horizontal as shown in FIGS. 4C and 4D, fluid 9, which has an n such that near objects will be in focus, fills the hollow lenticule and encompasses the light path. The range of downward tilt necessary for fluid 9 to fill the hollow lenticule can be adjusted by changing the relative amounts of fluids 9 and 10.

Figure 5A:
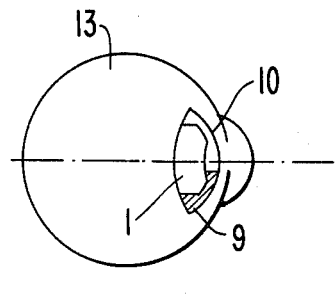
FIGS. 5A and 5B are schematic drawings showing the operation of the invention in the eye.
Figure 5B:
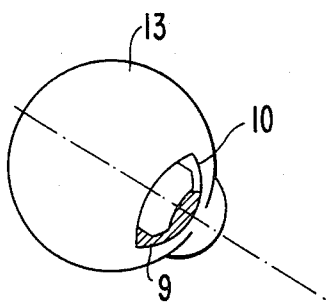

The operation of the lens in the eye is shown in FIG. 5. As the eye 13 moves in relation to the horizontal plane, the position of the lens is changed with respect to the horizontal. This changes the position of the fluid in the lenticule, thereby altering the power of the lens. Thus, as the position of the head changes, and therefore the position of the eye with respect to the horizontal changes, the power of the lens will change, allowing focus at either near or far points without accessory external lens.

Various fluids can be used to provide different n's. In the preferred embodiment, fluid 9 in the bottom of the lens is an organic oil, preferably silicone oil, and fluid 10 in the top of the lens is an aqueous solution, preferably saline solution. Fluid 10 could be a solution composed of any of those solutes that dissolve in water to provide a stable, transparent medium. Different sugars, such as sucrose and glucose, and many organic and inorganic salts would provide such a solution. In an alternative embodiment, fluid 10 can be air or another gas. Through the choice of fluids and the shape of the lens and the lenticule, the lens can be tailored to the needs of individual patients.

This invention is not limited to the use of only two fluids. Three or more fluids of different n's can be used to create a multipower, multifocus lens so that objects between near and distant ones will be more sharply in focus.

In still another embodiment, the lenticule, channels, and reservoirs can be filled with a single fluid, such as a transparent solution with a concentration gradient of solute. As the concentration of solute increases, the index of refraction of the solution also increases. For example, sodium chloride in water can be used. In this case, since the concentration of solute is greatest at the bottom of the lenticule, the index of refraction also will be greatest at the lower part of the lenticule. This system provides a gradual change in the index of refraction and eliminates lines in the field of vision due to light passing through immiscible materials with two different indices of refractions. Thus, this system is a variable focus lens.

Figure 6:
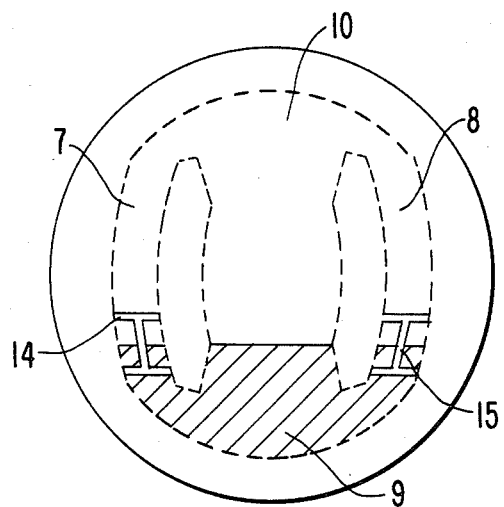
FIG. 6 is an anterior view of an alternative embodiment of the invention.

In yet another embodiment, pistons 14 and 15 are placed in channels 7 and 8 at the interface of the immiscible liquids as shown in FIG. 6. When the eye is moved upward or downward from the horizontal, gravity acting on such pistons facilitates the movement of the fluids through the channels, reservoirs, and lenticule. The pistons also prevent too great a shift in the fluids that could occur, for example, when the person in whom the lens has been implanted lies on his side. The pistons may be any shape, such as dumbell, rod, or ball-shaped, that expedites the movement of the fluids through the channels. Plastic pistons of about 0.25 mm in cross sectional diameter and resting at the fluid interface are preferred.

It will be apparent to those skilled in the art that various modifications and variations can be made in the present invention without departing from its scope or spirit. Thus, it is intended that the present invention cover the modifications and variations of this invention provided that they came within the scope of the appended claims and their equivalents.

What is claimed is:

1. A multifocus intraocular lens comprising:
   a body of transparent material suitable for permanent placement in the eye;
   a hollow lenticule in said body, said lenticule being positioned for encompassing the light path between the pupil of the eye and the retina;
   a pair of fluid reservoirs in said body, one above and one below said lenticule and in fluid communication therewith;
   channel means interconnecting said reservoirs, said channel means bypassing said light path and said lenticule, said channel means, lenticule, and reservoirs forming a closed system within said body; and
   transparent fluid means filling said closed system for changing the index of refraction of said lens upon predetermined changes in the inclination of said light path with respect to the horizontal, wherein said fluid means comprises at least two immiscible liquids with different refractive indices.

2. The lens as recited in claim 1 wherein said immiscible liquids with different refractive indices have a stable plane of separation, said plane lying just below the light path in the horizontal position thereof.

3. The lens as recited in claim 1 wherein one of said liquids is water and the other of said liquids is silicone oil.

4. A multifocus intraocular lens comprising:
   a body of transparent material suitable for permanent placement in the eye;
   a hollow lenticule in said body, said lenticule being positioned for encompassing the light path between the pupil of the eye and the retina;
   a pair of fluid reservoirs in said body, one above and one below said lenticule and in fluid communication therewith;
   channel means interconnecting said reservoirs, said channel means bypassing said light path and said lenticule, said channel means, lenticule, and reservoirs forming a closed system within said body;
   pistons located in said channel means; and
   transparent fluid means filling said closed system for changing the index of refraction of said lens upon predetermined changes in the inclination of said light path with respect to the horizontal.

5. The lens as recited in claim 4 wherein said fluid means includes two immiscible materials with different refractive indices and wherein said pistons float at the interface of said fluids.

6. A multifocus intracular lens comprising:
   a body of transparent material suitable for permanent placement in the eye;
   a hollow lenticule in said body, said lenticule being positioned for encompassing the light path between the pupil of the eye and the retina;
   a pair of fluid reservoirs in said body, one above and one below said lenticule and in fluid communication therewith;
   channel means interconnecting said reservoirs, said channel means bypassing said light path and said lenitcule, said channel means, lenticule, and reservoirs forming a closed system within said body; and
   transparent fluid means filling said closed system for changing the index of refraction of said lens upon predetermined changes in the inclination of said light path with respect to the horizontal, wherein said fluid means includes a transparent material of different density gradients.

7. The lens as recited in claim 6 wherein said transparent material is water with a salt dissolved therein.

8. The lens as recited in claim 7 wherein said salt is sodium chloride.

9. The lens as recited in claim 6 wherein said transparent material is water with sucrose dissolved therein.

* * * * *